(12) United States Patent
Kostka et al.

(10) Patent No.: US 6,200,961 B1
(45) Date of Patent: *Mar. 13, 2001

(54) CONCENTRATES OF ORGANOPHOSPHOROUS INSECTICIDES

(75) Inventors: Stanley J. Kostka, Cherry Hill; Rennan Pan, Plainsboro, both of NJ (US)

(73) Assignee: Aquatrols Corporation of America, Inc., Cherry Hill, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/212,994

(22) Filed: Dec. 16, 1998

(51) Int. Cl.[7] .................. A01N 57/00; A01N 25/00; A01N 65/00

(52) U.S. Cl. ............... 514/89; 424/196.1; 424/405; 424/DIG. 11; 514/75; 514/80; 514/82; 514/84; 514/85; 514/86; 514/87; 514/88; 514/90; 514/91; 514/92; 514/93; 514/94; 514/95; 514/98; 514/99; 514/102; 514/103; 514/104; 514/107; 514/108; 514/114; 514/118; 514/126; 514/127; 514/129; 514/131; 514/140; 514/141; 514/142; 514/143

(58) Field of Search .................. 424/601, 196.1, 424/405, DIG. 11; 514/75, 79, 80, 82, 84, 85, 86, 87, 88, 89, 90, 91, 92, 93, 94, 95, 98, 99, 102, 103, 104, 107, 108, 114, 118, 140, 141, 143, 147, 142, 148, 782, 783, 970, 975, 81, 126, 127, 129, 131, 772, 772.1, 772.3; 504/194, 195, 198, 199, 207, 208

(56) References Cited

U.S. PATENT DOCUMENTS

| 4,868,206 | 9/1989 | Hobbs ................... 514/457 |
| 4,952,401 | 8/1990 | Hobbs ................... 424/405 |
| 5,045,109 | 9/1991 | Nakamura et al. ........ 71/100 |
| 5,206,021 | * 4/1993 | Dookhith et al. ......... 424/405 |

FOREIGN PATENT DOCUMENTS

| 669 078 | 8/1995 | (EP) ............ A01N/25/02 |
| 670 113 | 9/1995 | (EP) ............ A01N/25/04 |
| 96/16539 | * 6/1996 | (WO) . |

* cited by examiner

*Primary Examiner*—John Pak
*Assistant Examiner*—Frank Choi
(74) *Attorney, Agent, or Firm*—John A. Shedden

(57) ABSTRACT

A low volatile organic compound co-solvent system is disclosed for preparing emulsion concentrates of low melting organophosphorous insecticides wherein the bioefficacy of the insecticide active is significantly enhanced. The co-solvent system comprises a water-soluble ethoxylated fatty acid/rosin acid-nonionic surfactant composition.

26 Claims, No Drawings

CONCENTRATES OF ORGANOPHOSPHOROUS INSECTICIDES

BACKGROUND OF THE INVENTION

1. Field of the Invention

The instant invention relates to bioefficaciously enhanced organophosphorous insecticidal formulations comprising the active and low volatile organic compound (low VOC) compositions; processes for preparing same; and methods of use.

2. Technology Description

Insecticides, miticides, aphicides, fungicides, bacteriocides, acaricides, nematicides (hereinafter these pesticides will be generically referred to for conciseness as "insecticides" as the term "insecticidally" will similarly represent generically miticidally, nematicidally, etc.) continue to be a group of products of immense agricultural and economic importance. Insecticides are expected to display ideal properties of a wide array including broad-spectrum activity concomitant with safety to beneficial insects, low mammalian and fish toxicity, and sufficiently long residual action yet with insignificant, harmless residue levels. In keeping with the above goals, it is desirable to utilize the minimum amount of insecticide necessary to achieve the required results. Therefore, formulation adjuvants that enhance the bioefficacy of the active and thus result in lower effective delivery amounts of the active to a locus are much sought after.

Many, if not most, insecticidal compounds are solid materials which have very low solubility in water. As a result, formulators are constantly using their ingenuity to find means for preparing these materials in stable formulations that can deliver maximum loading of active ingredient per unit volume to the end-user.

The most straight-forward approach to preparing concentrated liquid formulations with agrochemical actives, especially insecticides having limited aqueous solubility, has been through the use of aromatic organic solvent systems. In such systems, aromatic organic solvents such as xylene or kerosene are used to solubilize the pesticidal compound of interest.

Commonly, surfactants are also added to the insecticide-solvent compositions to form emulsions. The surfactant-emulsifiers interact with the insecticides in a number of ways both before and during actual use, i.e., application to the locus. The surfactants, often a pair of nonionic and anionic surfactants, can initially disperse and/or emulsify the insecticide in the solvent or in an inert carrier media and may also act as spreader, sticker, stabilizer, wetting agent, and defoamer. The surfactant composition may affect the rate of drying of a droplet on a surface and the nature of a residue liquid or crystal.

The presence of the volatile organic compounds in these formulations, together with the surfactants, enable stable emulsifiable insecticidal concentrates (EC's) to be prepared. Although such EC formulations have played and continue to play a major role in the insecticidal market, they have a significant drawback in that the formulations are commonly based on the use of considerable quantities of highly volatile organic compounds (high VOC's). These high VOC's create both toxicological and ecotoxicological problems. As a result, many government agencies such as the United States Environmental Protection Agency and the European Economic Community Council are proposing legislation and many countries such as Germany and Canada are now requiring eco-labeling of formulations which contain high VOC's.

Thus, to reduce not only the deleterious effects upon the environment, but also the potential for hazardous worker exposure situations, especially in closed environments such as greenhouses, agricultural/chemical manufacturers and formulators continually seek ways to deliver highly loaded, stable insecticidal formulations to the end-user with significantly reduced levels of high VOC's and preferably without their presence.

To avoid the use of high VOC's in certain pesticidal formulations and to obtain slightly increased pesticidal loadings, Lubetzky, et al. in EP publication numbers 669,078 and 670,113 have disclosed the use of rosin and rosin derivatives that are insoluble in water to "plasticize" certain pesticides and thus to prepare pesticidal emulsions in water (EW's) and emulsifiable concentrates (EC's).

Applicants, in copending Provisional Application Ser. No. 60/070,101 filed Dec. 30, 1997, the disclosure of which is hereby incorporated by reference, relates to the discovery of extremely stable, highly loaded water soluble, low VOC pesticidal emulsion concentrates comprising a) a pesticide having a melting point of 110° C. or less; b) an alkoxylated fatty acid and rosin acid composition having from greater than 25 to about 60 weight percent alkoxylated rosin acids and from about 40 to less than 75 weight percent alkoxylated fatty acids with about 9 to 20 alkoxy moieties per molecule of acid; and c) at least one nonionic surfactant. It was discovered that the aforedescribed ethoxylated acid compositions possess very unique solvent characteristics with respect to certain relatively water insoluble pesticides.

SUMMARY OF THE INVENTION

The instant invention relates to the discovery that certain alkoxylated fatty/rosin acid formulations can not only provide extremely stable, highly loaded solvent systems for specific organophosphorous insecticidal compounds, but that these formulations can also significantly enhance the bioefficacy of these insecticidal compounds.

DETAILED DESCRIPTION OF THE INVENTION

It has been discovered that not only do certain water-soluble fatty acid/rosin acid ethoxylate compositions possess unique solvent characteristics with respect to low melting organophosphorous insecticidal compounds, but also that these adjuvant compositions significantly enhance the bioefficacy of the organophosphorous active. A preferred method of preparing emulsion concentrates of these components is to melt the organophosphorous insecticide and dissolve same in the highly alkoxylated mixture of the fatty acids and rosin acids; preferably a tall oil mixture.

Organophosphorous compounds are antichlolinesterase chemicals which damage or destroy chlolinesterase, the enzyme required for nerve function in the animal body. Organophosphorous insecticides, owing primarily to their ester nature, offer fundamental advantages in that they can be easily degraded hydrolytically, enzymatically, or biologically.

Organophosphorous compounds including those disclosed in U.S. Pat. No. 3,244,586 and specifically those with a halogen substitution, are known to be extremely useful as insecticides and are especially adapted to be employed as active toxicants in compositions for the control of a number of mite, insect, bacterial, and fungal organisms, such as beetles, ticks, worms, aphids, flies, roaches, cattle grubs, screw worms, trash fish, snails, ascarids, nematodes, roundworms, and *Rhizoctonia solani* (a plant pathogenic fungus).

The organophosphorous insecticides of the instant invention are preferably the phosphorothioates, phosphorodithioates, phosphoroamidates, phosphoroamidothioates, and phosphonothioates which have melting points below about 120° C.

More preferably, the organophosphorous compounds are of the following formulas:

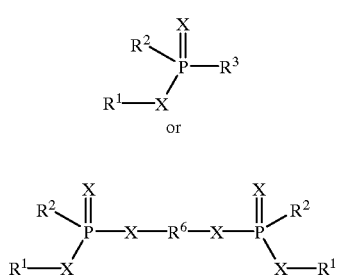

wherein X is each individually O or S;

$R^1$ is substituted or unsubstituted, branched or unbranched lower alkyl, aryl, or aralkyl;

$R^2$ is $XR^1$ or $R^1$;

$R^3$ is $XR^4$ or $NHR^5$;

$R^4$ is substituted or unsubstituted lower alkyl, lower alkylene, vinyl, aryl, aralkyl, cyanoaryl, carboalkoxyalkyl, alkoxyalkyl, alkoxyaryl, alkoxycarbonylalkyl, aminocarbonylalkyl, alkylcarbamoylalkyl, alkylthioalkyl, or alkylthioaryl;

$R^5$ is H, acetyl, or lower alkyl; and $R^6$ is lower alkyl, dioxanyl, or thiodi-p-phenylene wherein, in the specification and claims of this disclosure "aryl" includes heteroaryl compounds and "substituted" includes halogen substitutions. Also, in the present specification and claims, the term "lower alkyl" and "lower alkoxy" refer to radicals of from 1 to 8 inclusive, carbon atoms.

Much more preferably, the aryl radicals are selected from the group consisting of substituted or unsubstituted phenyl, pyridinyl, pyrimidinyl, cyanophenyl, alkylthiophenyl, benzotriazinyl, phthalimidinyl, oxobenzoxazolyl, oxothiadiazolyl, carbalkoxybenzyl, morpholinocarbonylalkyl, nitrophenyl, oxobenzopyranyl, quinolyl, pyridazinyl, pyrazinyl, quinoxalinyl, pyrazolyl, triazolyl, and thiadiazolinonyl.

The most preferred insecticides of the instant invention are selected from the group consisting of:

O,O-diethyl O-3,5-dibromo-6-chloro-2-pyridyl phosphorothioate,

O,O-diethyl O-3,5,6-trichloro-2-pyridyl phosphorothioate,

O,O-diethyl O-3,4,5,6-tetrachloro-2-pyridyl phosphorothioate,

O,O-diethyl O-3,4,6-trichloro-2-pyridyl phosphorothioate,

O,O-(thiodi-4,1-phenylene)bis(O,O-dimethyl phosphorothioate),

O,6-ethoxycarbonyl-5-methyl pyrazolo[1,5-a]pyrimidi-N-2-yl O,O-diethyl phosphorothioate, O-(4-bromo-2,5-dichlorophenyl)O,O-diethyl phosphorothioate, O,O-dimethyl-O-(2,5-dichloro-4-iodophenyl) phosphorothioate, O,O-diethyl O-2-quinoxalinyl phosphorothioate O-2,6-dichloro-4-methyl phenyl O,O-dimethyl phosphorothioate, O,O-diethyl S-carboethoxymethyl phosphorodithioate, O,O-diethyl S-[(4-oxo-1,2,3-benzotriazin-3(4H)-yl) methyl]phosphorodithioate, O,O-dimethyl S-[(4-oxo-1,2,3-benzotriazin-3(4H)-yl) methyl]phosphorodithioate, S-(2-(formyl methyl aminol)-2-oxoethyl)O,O-dimethyl phosphorodithioate, O,O-dimethyl phosphorodithioate, S-ester with 4-(mercaptomethyl)-2-methoxy-1,3,4-thiadiazolin-5-one, O-ethyl S,S-dipropyl phosphorodithioate O,O-diethyl-S-(N-isopropyl carbamoyl methyl) phosphorodithioate O,O-dimethyl S-(2-((1-methyl carbamoyl ethyl)thio) ethyl)phosphorodithioate, O,S-dimethyl N-acetyl phosphoroamidolhioate, O,O-bis(p-chlorophenyl)acetimidoyl-phosphoroamidothioate, O,S-dimethyl phosphoroamidothioate, O-butyl O-3,5-dichloro-2-pyridyl methyl phosphoroamidothioate, O-isopropyl O-3,5-dichloro-2-pyridyl methyl phosphoroamidothioate, O-sec-butyl O-3,5-dichloro-2-pyridyl methyl phosphoroamidothioate, O-isobutyl O-3,5-dichloro-2-pyridyl methyl phosphoroamidothioate, O-methyl O-3,5,6-trichloro-2-pyridyl isopropyl phosphoroamidothioate, O-methyl O-3,5-dibromo-2-pyridyl isopropyl phosphoroamidothioate, O-methyl O-3,5-dichloro-2-pyridyl isopropyl phosphoroamidothioate, O-methyl O-3,5-dibromo-2-pyridyl methyl phosphoroamidothioate, O-ethyl O-3,5-dibromo-2-pyridyl methyl phosphoroamidothioate, O-ethyl O-3,5-dichloro-2-pyridyl methyl phosphoroamidothioate, O-methyl O-3,5-dichloro-2-pyridyl methyl phosphoroamidothioate, O-methyl O-3,5-dichloro-2-pyridyl ethyl phosphoroamidothioate, O-ethyl O-3,5-dichloro-2-pyridyl-ethyl phosphoroamidothioate, O-isopropyl O-3,5-dibromo-2-pyridyl methyl phosphoroamidothioate, O-propyl O-3,5-dichloro-2-pyridyl methyl phosphoroamidothioate, O-propyl O-3,5-dichloro-2-pyridyl propyl phosphoroamidothioate, O-methyl O-3,4,6-trichloro-2-pyridyl isopropyl phosphoroamidothioate, propyl 3,5,6-trichloro-2-pyridyl methyl phosphoroamidate, methyl 3,5,6-trichloro-2-pyridyl isopropyl phosphoroamidate, O-p-cyanophenyl O-ethyl phenyl-phosphonothioate, O-ethyl O-(4-nitro phenyl)phenyl phosphonothioate, and O-ethyl S-phenyl ethyl phosphonodithioate.

The very most preferred insecticide for use in the instant invention is O,O-diethyl O-(3,5,6-trichloropyridine-2-yl) phosphorothioate also known as chlorpyrifos.

These aforelisted organophosphorous compounds are known to be very effective for the control of many parasitic organisms, particularly those found on the roots or aerial portions of growing plants inclusive of aphids, mites, plant pathogens, and insects. These compounds are effective at low concentrations, against chewing and sucking types of insects, such as southern armyworm (*Prodenia eridania*), California red scale (*Aonidiella aurantil*), and Mexican bean beetle (*Epilachna varivestis*). They are also extremely useful for the impregnation of soil in nematocidal concentrations for the control of nematodes such as root-knot nematode. An additional advantage to the use of these compounds is that they can be applied to soil in and around growing vegetation in amounts required for pest control without significant injury to plants.

Furthermore, as a result of the high level of insecticidal activity of these compounds, only a few pounds, e.g., from about 0.25 to about 5 pounds, of active ingredient per acre per application is usually the recommended use rate.

The organophosphorous compounds which are particularly useful in this invention are those that have melting points below about 120° C.; preferably below about 110° C.; and most preferably below about 90° C.

To form the enhanced, bioefficacious emulsion concentrates of this invention, the aforementioned solid insecticides are melted and dissolved in a low VOC water-soluble solvent prepared by highly alkoxylating a mixture of fatty acids and rosin acids; preferably a tall oil mixture.

The primary fatty acids useful in the process of this invention are the $C_{14}$ to $C_{20}$ unsaturated acids, especially the fatty acids selected from the group consisting of oleic, linoleic, conjugated linoleic acids, palmitic, stearic, and mixtures thereof.

The primary rosin acids useful in the process of this invention are the $C_{19}$–$C_{20}$ aromatic acids, especially the rosin acids selected from the group consisting of abietic, neoabietic, dehydroabietic, tetrahydroabietic, palustric, pimaric acids and mixtures thereof.

The final acid compositions, whose components are subsequently alkoxylated either prior to being mixed together to form the composition or after the acid composition mixture is present, comprise from greater than about 25 to about 60 weight percent alkoxylated rosin acids, preferably from 30 to 40 weight percent alkoxylated rosin acid; and from about 40 to less than about 75 weight percent, preferably from about 60 to about 70 weight percent fatty acids; all of the above acid weight percents based on the total weight of the alkoxylated fatty acids and rosin acids composition.

The water-soluble alkoxylated compositions should contain an average molar addition of from about 6 to about 20 alkoxy moieties per molecule of acid; preferably from about 9 to about 16.

As noted above, although the rosin acids can be obtained individually from natural products such as wood and gum resins and the fatty acids can be obtained individually, for example, from natural oils and fats such as olive oil, peanut oil, butter fat, cottonseed, soybean and so on, the fatty acid/rosin acid compositions of this invention are preferably obtained from certain tall oil products.

The pine tree is the source of tall oil which is liberated when wood is converted to paper pulp by the sulfate or Kraft process. During the pulping process, an alkaline digestion liquor ("black liquor") is washed out of the pulp. Rosin soaps and fatty acid soaps are skimmed off of this black liquor and acidification releases free rosin and fatty acids. This mixture was originally called Tallolja (Swedish for pine oil) and the term "tall oil" was eventually adapted as a standard by the United States.

The fatty acids in crude tall oil typically consist mainly of a mixture of oleic acid [40.0%][$CH_3(CH_2)_7CH=CH(CH_2)_7COOH$]; linoleic acid [32.0%][$CH_3(CH_2)_4CH=CHCH_2CH=CH(CH_2)_7COOH$]; linoleic acid, conjugated (includes higher molecular weight polyunsaturated acids) [10.0%][$CH_3(CH_2)_4CH_2CH=CH\ CH=CH(CH_2)_7COOH$]; palmitic acid [6.5%][$CH_3(CH_2)_{14}COOH$]; and stearic acid [2.0%][$CH_3(CH_2)_{16}COOH$]. Also present are palmitoleic acid [1.5%]; and to a small extent, higher molecular weight saturated acids such as arachidic ($C_{20}$), behinic ($C_{22}$), lignoceric ($C_{24}$) and cerotic ($C_{26}$) acids, $C_{20}$ and higher molecular weight unsaturated and polyunsaturated acids, and small amounts of low boiling point monobasic and dibasic acids.

The rosin acids in crude tall oil are similar to those occurring in wood and gum rosin and typically consist mainly of abietic acid [30–40%] in equilibrium with its isomer neoabietic acid [4–20%], palustric acid [7%], dehydroabietic acid [5–17%], pimaric acid [8–16%], with dehydroabietic and tetrahydroabietic acids comprising 2 to 28%.

The fatty acid/rosin acid compositions of this invention are alkoxylated, i.e., polyoxyalkylene esters are prepared, by using art-recognized, standard condensation techniques readily available; known to those skilled in the art; and described in numerous publications, for example, on pages 142 to 170 of chapter 5 of the book "Nonionic Surfactants" by W. B. Satkowski, S. K. Huang, and R. L. Liss, edited by M. J. Schick, Lever Bros. Co. Research Center, Edgewater, N.J. (Marcel Dekker, Inc., New York). Typical procedures are set forth in U.S. Pat. Nos. 2,586,767 and 2,610,966.

The organic carboxylic acids may be either directly esterified with alkylene oxide or through a reaction with polyalkylene glycol intermediates. The alkylene oxides which may be used to prepare the nonionic monofunctional polyoxyalkylene esters or polyalkylene glycol intermediates include ethylene oxide, propylene oxide and butylene oxide. Tetrahydrofuran may also be used. Preferred alkylene oxides are ethylene oxide and propylene oxide. When both of these oxides are utilized, they may be added simultaneously or in sequence to prepare statistic or block polymer surfactants. The alkylene oxides, for example, ethylene oxide, may also be used alone.

The nonionic surfactants useful in the formulations of this invention must have significant solubility in water. The H.L.B. of the nonionic surfactants should preferably be in the solubilizer/wetting agent range of from about 12 to about 20.

Examples of such nonionic materials are the following:
1) block-polymeric polyether glycols obtained, for example, by the addition of ethylene oxide on a condensation product of propylene oxide with propylene glycol;

2) alkoxylated alkyl phenols, i.e., alkylphenol-polyalkylene oxide condensates which are condensation products of alkylphenols with at least one alkylene oxide;
3) alkoxylated triglycerides;
4) alkoxylated di- or tri-styryl phenols;
5) alkoxylated sorbitol fatty esters;
6) condensation products of aliphatic alcohols with at least one alkylene oxide;
7) condensation products of ethylene oxide with the products resulting from the reaction of propylene oxide and ethylene diamine;
8) ammonia, monoethanol and diethanol amides of acyl fatty acids, wherein the acyl moieties are normally derived from naturally occurring glycosides, but can be derived synthetically;
9) various semi-polar, long chain nonionics including:
   i) tertiary amine oxides,
   ii) tertiary phosphine oxides; and
   iii) sulfoxides;
10) polysiloxanes, preferably the alkoxylated polysiloxanes; and
11) mixtures thereof.

The preferred nonionic surfactants are the condensation products of aliphatic alcohols with at least one alkylene oxide and the alkoxylated alkyl phenols, especially the aliphatic ethoxylates and the alkylphenol polyethoxylates; the alkoxylated triglycerides such as ethoxylated and ethoxylated-propoxylated castor oil; and the alkoxylated sorbitol fatty esters. Most preferred are the aliphatic alcohol ethoxylates which are aliphatic alcohol polyethylene oxide condensates of aliphatic alcohols wherein the aliphatic chain contains from about 4 to about 20, preferably about 5 to about 12 carbon atoms in either a straight chain or branched chain configuration and condensed with ethylene oxide, the said ethylene oxide being present in amounts equal to 2 to 50 moles of ethylene oxide per mole of aliphatic alcohol; preferably 5 to 25, most preferably 8–15. The aliphatic alcohol may be of primary, secondary or tertiary structure; preferably of a secondary structure. The most preferred alcohol ethoxylate is an ethoxylated trimethyl secondary nonanol.

Examples of the ethoxylated alkyl phenols include nonyl phenol condensed with about 9.5 moles of ethylene oxide per mole of nonyl phenol; dodecylphenol condensed with about 12 moles of ethylene oxide per mole of phenol, diamyl phenol condensed with about 9 moles of ethylene oxide per mole of phenol; dinonyl phenol condensed with about 15 moles of ethylene oxide per mold of phenol; and diisooctyl phenol condensed with about 15 moles of ethylene oxide per mole of phenol. Commercially available nonionic surfactants of this type include the IGEPAL series of nonionics, e.g., those sold under the trademarks CO-630 and DAP-9 by Rhone-Poulenc Inc.

Illustrative of the preferred polysiloxanes are those of the formula:

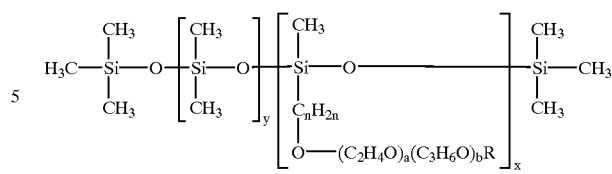

wherein n is from about 2 to about 6; a is from about 8 to about 25; and b is from 0 to about 25; and the oxyalkylene groups may be random or block mixtures; y is from 0 to about 5; x is from about 1 to about 5; and R is selected from the group consisting of hydrogen, $C_1$–$C_4$ alkyl, and a $C_1$–$C_4$ alkyl ester; or

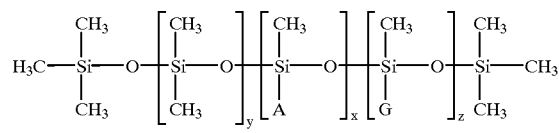

wherein A is a linear or branched alkyl having about 6 to about 30 carbon atoms;
G is a glycol moiety of the formula —R'(OCH$_2$CH$_2$)$_m$OR" wherein R' is a divalent alkylene group having about 2 to about 6 carbon atoms; R" is selected from the group consisting of hydrogen, $C_1$–$C_4$ alkyl, and a $C_1$–$C_4$ alkyl ester; m is about 8 to about 100; y is 0 to about 5; X is about 0.1 to about 2.5; and z is about 0.1 to about 5.0.

The primary components of the low VOC water-soluble, pesticidal emulsion concentrates of the instant invention have the following concentration ranges: the pesticide is present from 10 to 60 weight percent, preferably from 10 to 40 weight percent; the ethoxylated fatty acid/rosin acid mixture from 20 to 60 weight percent, preferably from 30 to 55 weight percent; and the nonionic surfactant from 15 to 45 weight percent, preferably from 20 to 40 weight percent; all weight percents being based on the total weight of the emulsion concentrate.

The liquid pesticide, ethoxylated fatty acid/rosin acid mixture, and nonionic surfactant concentrates, i.e., the water-soluble, low VOC compositions of this invention, can be used to prepare stable oil-in-water emulsions. When these emulsions in water (EW's) are desired, the preferred concentration ranges of the components based on the total weight of the aqueous emulsion are as follows: the pesticide should be present from 1 to 50 weight percent; the alkoxylated fatty acid/rosin acid composition should be present from 2 to 55 weight percent; and the nonionic surfactant from about 1.5 to 35 weight percent. The water can be present up to about 78 weight percent.

The ability of the concentrates of this invention to form stable emulsions when diluted with water is especially important for the solution stability allows for a homogeneous distribution of active ingredients on application targets, which assists in enhancing biological efficacy.

The agrochemical compositions according to the invention may optionally comprise:
a) an anionic surfactant, such as i) partial sulfate and phosphate esters of polyoxyalkylene or (ii) carboxylate surfactants and their salts; and/or b) other nonionic surfactants, for example, polyoxyalkylene ethers of aliphatic alcohol having from 6 to 30, preferably from 10 to 20, and more particularly from 12 to 16 carbon atoms in the aliphatic residue; and/or c) a long chain carboxylic acid having from 10 to 25 carbon atoms such as caproic acid, caprylic acid, capric acid, lauric acid, myristic acid, palmitic acid, palmitoleic acid, margaric acid, stearic acid, oleic acid, linoleic acid, linolenic acid, and arachidic acid; and/or d) a lower alkanol ester of a long chain $C_{10}$–$C_{22}$ carboxylic acid, such as, for example, oleic, linoleic, linolenic, stearic, myristic, and palmitic acids; and/or e) an acidulated soap stock, said soap stock being a by-product of alkali refining of crude vegetable or animal fats and oils such as oils extracted from soybeans, canola, corn, cottonseed, olives, sunflower, safflower, sesame, peanut, rapeseed and rice; acidulated soybean soapstock being the preferred soapstock.

The insecticidal compositions of this invention may also comprise anti-freezing agents, anti-foam agents, compatibility agents, oxidation and U.V. protectants, bactericides, and pH buffering agents. Anti-foam agents decrease and/or prevent foaming when the solution containing the pesticidally-active formulation is agitated or sprayed. Compatibility agents function to allow and maintain an emulsification of two or more ingredients that would otherwise separate when mixed. Buffering agents function to moderate the pH of the water in the tank solution.

The concentrated formulations of this invention can be prepared preferably by melting one or more of the water-insoluble pesticidally-active ingredients and physically blending this molten material with the alkoxylated fatty acid/rosin acid solvent. The nonionic surfactant composition and any optional ingredients are then added to the mixture using standard emulsion preparation methods well known in the art. The sequence of addition is not a critical feature of the invention. Furthermore, the ingredients can also be premixed prior to the application of heat.

In carrying out the methods of the present invention, the undesirable pests can be controlled by contacting the organism, its habitat, and/or its food supply prior to ingestion with an insecticidally effective amount of a formulation comprising the emulsion concentrates of this invention containing the organophosphorous active. The term "comprising the emulsion concentrate(s)" is meant to include the emulsion concentrate(s) of this invention neat or after being diluted with water. These liquid formulations can be applied to living plants without substantial injury to the foliage thereof. When the compositions of the instant invention are applied as emulsion concentrates, the toxicant can be present in a concentration of from about 10 to about 60 percent by weight based on the total weight of the emulsion concentrate.

The exact concentration of the organophosphorous insecticide employed in an aqueous emulsion for application to the pest, its habitat or food can vary provided an insecticidal dosage of toxicant is supplied either on the organism or its environment, or in its food. This dosage of toxicant is primarily dependent upon the susceptibility of a particular organism to the specific organophosphorous compound. The emulsion concentrates of this invention are readily dispersible in water to form sprays containing the active toxicant in any commercially desired amount. Good results are obtained with the aqueous emulsion concentrates of this invention so diluted with water to form, for example, spray mixtures that the toxicant is present in the final diluted aqueous composition from about 0.5 to 2000 parts or more by weight per million.

Other than in the operating examples, or where otherwise indicated, all numbers expressing quantities of ingredients or reaction conditions used herein are to be understood as modified in all instances by the term "about".

The following examples serve to illustrate, but not limit, the invention. All parts and percentages are by weight, unless otherwise noted.

EXAMPLE I

Rosin acid-fatty acid (RFA) compositions having approximately the following composition: abietic acid (21–22 weight percent), palustric acid (2–3 weight percent), pimaric acid (7–8 weight percent), various isomers of the abietic, palustric and primaric acids and similar cyclic acids (6–7 weight percent), oleic acid (15–16 weight percent) linoleic acid (11–12 weight percent), isomers of $C_{18}$–$C_{19}$ and $C_{20}$ acids (9–10 weight percent), and higher fatty acids (17–18 weight percent) are ethoxylated such that ethoxylated rosin acid-fatty acid compositions are prepared having a molar addition of approximately 16 ethylene oxide moieties per molecule of acid.

Technical chlorpyrifos, a solid, organophosphorous insecticide, i.e., O,O-diethyl O-(3,5,6-trichloro-2-pyridyl)-phosphorothioate, is blended with the above-described alkoxylated rosin acid-fatty acid composition together with a secondary alcohol ethoxylate, i.e., TERGITOL TMN-6 non and surfactant, a trademark of Union Carbide for an ethoxylated trimethyl nonanol.

The mixture is heated in an oven to above the melting point of the chlorpyrifos, i.e., in the range of from about 41.5 to about 43.5° C. After the insecticide is melted, the sample is well agitated and subsequently cooled to room temperature.

The low VOC, emulsifiable concentrate has the following formulation (in weight percent based on the total formulation weight):

| | |
|---|---|
| Rosin Acid/Fatty Acid Ethoxylate | 53.2 weight percent |
| Chlorpyrifos | 25.5 weight percent |
| TERGITOL TMN-6 surfactant | 21.3 weight percent |

EXAMPLE II

The low VOC, emulsifiable chlorpyrifos concentrate of Example I is diluted with water to form an aqueous spray composition having about 2 pounds of chlorpyrifos per gallon of diluted composition hereinafter identified as Chlorpyrifos 2E.

Field evaluations are conducted from June 19 through July 17 using replicated field plots. The target pest during this early season trial is the Tawny Mole Cricket. The Chlorpyrifos 2E formulation of the instant invention is applied at 1, 2, and 3 pounds of active ingredient per acre. For comparison purposes, DURSBAN 4E insecticide formulation, a commercial chlorpyrifos insecticide formulation sold by The Dow Chemical Company is also applied at 1, 2, and 3 pounds of active ingredient per acre. Also for comparison purposes, ORTHENE 75S insecticide formulation, an acephate, i.e., O,S-dimethyl acetyl phosphoramidothioate insecticide formulation sold by the Valent U.S.A. Corp. is applied at 2.25 pounds active ingredient per acre. Control data, i.e., non-treated plot data is also monitored.

Mole Cricket damage ratings are determined prior to the treatment applications and subsequently at 1–2 week intervals. Treatments are applied with standard research plot equipment. The results of these trials are as indicated in Table 1.

TABLE 1

Efficacy of Chlorpyrifos 2E Formulations on Early Season Control of Tawny Mole Cricket (St. Simons Island, GA)

| | ai/acre* | 19-June | 26-June | 3-July | 17-July |
|---|---|---|---|---|---|
| Low VOC | 1 | 3.72 a** | 1.88 bcd | 2.20 bc | 3.13 cd |
| Low VOC | 2 | 3.70 a | 1.48 c–f | 1.575 cde | 1.90 fg |
| Low VOC | 3 | 3.60 a | 0.58 fg | 0.305 gh | 0.65 h |
| Dursban | 1 | 3.63 a | 3.33 a | 3.33 a | 4.05 ab |
| Dursban | 2 | 3.70 a | 2.25 bc | 1.60 cde | 2.65 def |
| Dursban | 3 | 3.63 a | 2.27 bc | 1.25 def | 1.65 g |
| Control | 0 | 3.45 a | 3.50 a | 3.50 a | 4.38 a |
| Orthene 75S | 2.25 | 3.55 a | 1.83 bcd | 1.55 cde | 1.85 fg |

*ai/ac = lbs. ai/ac
**Means in columns followed by the same letter are not significantly different (P = 0.05)

The low VOC Chlorpyrifos 2E formulations of the instant invention consistently reduce Mole Cricket damage better than the commercial 4E DURSBAN insecticide formulation when applied at the same rate. More importantly, the low VOC Chlorpyrifos 2E formulation applied at the 2.0 lb. ai/acre rate, while using one-third less active ingredient, is as efficacious as the 3.0 lb. ai/acre treatment rate of the commercial DURSBAN insecticide formulation. Furthermore, at 3.0 lb. ai/acre, the low VOC Chlorpyrifos 2E formulation is significantly more efficacious than the same treatment rate of the commercial DURSBAN 4E insecitide formulation.

EXAMPLE III

Field evaluations are conducted with the Chloripyrifos 2E of Example II from September 18 through October 23 using replicated field plots. The target pest is the 3rd to 5th instars of the Southern Masked Chafer. The Chloripyiifos 2E formulation of the instant invention is applied at 2 and 3 pounds of active ingredient per acre. For comparison purposes, DURSBAN 4E chlorpyrifos insecticide formulation is also applied at the identical rates of 2 and 3 pounds of active ingredient per acre. Control data, i.e., non-treated plot data is also monitored.

The live grub damage ratings are determined prior to treatment application and subsequently at 1–2 week intervals. Treatments are applied with standard research plot equipment. The results of these trials are as indicated in Table 2.

TABLE 2

Efficacy of Chlorpyrifos 2E on $3^{rd}$–$5^{th}$ Instars of Southern Masked Chafer (St. Simons Island, GA)

| | ai/acre | 18-September | 25-September | 2-October | 9-October | 23-October |
|---|---|---|---|---|---|---|
| Low VOC | 2 | 46.33 a | 25.27 bcd | 38.83 ab | 25.00 ab | 24.60 ab |
| Low VOC | 3 | 56.07 a | 17.83 d | 12.67 cd | 14.93 bc | 8.90 bc |
| Dursban | 2 | 45.20 a | 37.30 a–d | 38.80 ab | 33.93 ab | 29.47 ab |
| Dursban | 3 | 60.27 a | 41.97 a–d | 42.33 ab | 35.03 ab | 35.03 a |
| Control | 0 | 46.33 a | 43.50 ab | 42.57 ab | 44.60 a | 42.57 a |

The most effective chlorpyrifos formulation evaluated at this test location is the low VOC Chloripyrifos 2E formulation of the instant invention. Numbers of live larvae are significantly lower in plots receiving the 3.0 lb. ai/acre treatment rate of the low VOC formulation. Neither the 2 nor the 3 pound per acre treatment rates of the DURSBAN chlorpyrifos formulation provides commercially acceptable larvae control.

EXAMPLES IV–VI

Field evaluations on the late season control of Tawny Mole Crickets are conducted using replicated field plots in Georgia at Savannah, from September 3 through October 1; at St. Mary's from September 12 through October 17; and at St. Simons Island from September 18 through October 16. The Chlorpyrifos 2E formulation of the instant invention is applied at 2 and 3 pounds of active ingredient per acre. For comparison purposes, DURSBAN 4E Chlorpyrifos insecticide formulation is also applied at the identical rates of 2 and 3 pounds of active ingredient per acre. Also for comparison purposes, ORTHENE 75S acephate insecticidal formulation is applied at 2.25 pounds of active ingredient per acre. Control data, i.e., non-treated plot data is also monitored.

Tawny Mole Cricket damage ratings are determined as in Example II. Treatments are applied with standard research plot equipment. The results of these trials are as indicated in Tables 3 through 5.

TABLE 3

Efficacy of Chlorpyrifos 2E on Late Season Control of Tawny Mole Cricket
(St. Mary's, GA)

|  | ai/acre | 12-September | 26-September | 3-October | 17-October |
| --- | --- | --- | --- | --- | --- |
| Low VOC | 2 | 3.93 ab | 1.50 cde | 0.87 def | 0.97 e |
| Low VOC | 3 | 3.90 ab | 0.27 g | 0.47 f | 0.80 e |
| Dursban | 2 | 3.20 c | 2.67 b | 2.40 b | 2.57 b |
| Dursban | 3 | 4.13 a | 1.63 cde | 1.40 cd | 1.60 cde |
| Orthene 75S | 2.25 | 3.93 ab | 1.10 def | 0.70 def | 2.03 bcd |
| Control | 0 | 3.70 abc | 6.70 a | 7.20 a | 7.17 a |

TABLE 4

Efficacy of Chlorpyrifos 2E on Late Season Control of Tawny Mole Cricket
(Savannah, GA)

|  | ai/acre | 3-September | 10-September | 17-September | 1-October |
| --- | --- | --- | --- | --- | --- |
| Low VOC | 2 | 5.53 a | 2.10 def | 1.90 ef | 2.57 ef |
| Low VOC | 3 | 5.80 a | 1.10 f | 1.10 f | 1.43 g |
| Dursban | 2 | 6.07 a | 4.50 b | 5.20 b | 5.63 b |
| Dursban | 3 | 5.87 a | 4.03 bc | 4.10 bc | 4.50 cd |
| Orthene 75S | 2.25 | 5.47 a | 1.13 f | 2.13 ef | 2.30 efg |
| Control | 0 | 5.40 a | 6.10 a | 7.30 a | 9.00 a |

TABLE 5

Efficacy of Chlorpyrifos 2E on Late Season Control of Tawny Mole Cricket
(St. Simons Island, GA)

|  | ai/acre | 18-September | 25-September | 2-October | 16-October |
| --- | --- | --- | --- | --- | --- |
| Low VOC | 2 | 3.87 abc | 1.73 de | 1.90 de | 1.03 c–f |
| Low VOC | 3 | 3.60 bc | 0.77 f | 1.07 f | 0.30 f |
| Dursban | 2 | 3.87 abc | 2.87 b | 3.50 b | 2.5 b |
| Dursban | 3 | 3.87 abc | 1.97 cde | 2.43 cde | 1.67 b–e |
| Orthene 75S | 2.25 | 4.40 a | 1.17 ef | 1.90 de | 0.83 def |
| Control | 0 | 3.90 abc | 5.27 a | 6.03 a | 7.23 a |

With respect to the control of late instar Mole Cricket nymphs and adults in the plots at St. Mary's, Georgia, both the treatments, i.e., the 2 and 3 pounds ai/acre of the low VOC Chlorpyrifos 2E formulations of the instant invention provide significantly better control than one achieves by similar rates with the commercial DURSBAN 4E chlorpyrifos insecticidal formulation.

The 3.0 lb. ai/acre low VOC Chlorpyrifos 3E formulation is significantly more efficacious than the 2.0 lb./acre treatment rate. The 2.0 lb. ai/acre treatment by the Chlorpyrifos 2E formulation of the instant invention is equivalent to the 3.0 lb. ai/acre rate of the commercial DURSBAN formulation. While the commercial DURSBAN formulation significantly reduces mole cricket damage as compared to the untreated control, performance is inferior to the low VOC Chlorpyrifos 2E formulation. Similar results are obtained at the other two locations where the low VOC chlorpyrifos formulations of the instant invention are evaluated.

In summary, the results of the trials as reported in Examples II–VI clearly indicate that the low VOC organophosphorous formulations of the instant invention significantly enhance the control of pests, especially soil inhabiting insect pests while concomitantly reducing pesticide application rates, worker exposure to applied materials levels, and the overall pesticide loadings on the environment.

Although the invention is described with respect to specific modifications, the details thereof are not to be construed as limitations except to the extent indicated in the following claims.

What is claimed is:

1. An organophosphorous insecticidal emulsion concentrate consisting essentially of:

a) from about 10 to about 60 percent by weight of an organophosphorous insecticide having a melting point of less than about 120° C.;

b) from about 20 to about 60 percent by weight of a water-soluble alkoxylated acid composition wherein said acid composition comprises:
  i) from greater than about 25 to about 60 percent by weight alkoxylated rosin acids; and
  ii) from about 40 to less than about 75 percent by weight alkoxylated fatty acids wherein the rosin acids and fatty acids have an average molar addition of from about 6 to about 20 alkoxy moieties per molecule of acid; the weight percents of the rosin and fatty acids being based on the total weight of said alkoxylated acids; and c) from about 15 to about 45 percent by weight of nonionic surfactant other than said alkoxylated rosin and alkoxylated fatty acids wherein said concentrate is essentially free of volatile organic compounds; and wherein the weight percents are based on the total weight of the emulsion concentrate except where indicated.

2. The emulsion concentrate of claim 1 wherein the organophosphorous insecticide is selected from the group consisting of:
  i) phosphorothioates;
  ii) phosphorodithioates;
  iii) phosphoroamidates;
  iv) phosphoroamidothioates; and
  v) phosphonothioates.

3. The emulsion concentrate of claim 1 wherein the organophosphorous insecticide is a compound of the formula:

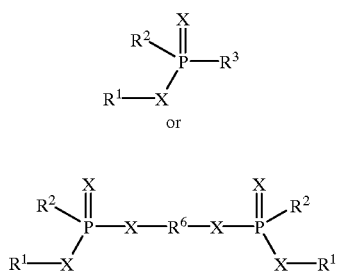

wherein X is each individually O or S;
$R^1$ is substituted or unsubstituted, branched or unbranched lower alkyl, aryl, or aralkyl;
$R^2$ is $XR^1$ or $R^1$;
$R^3$ is $XR^4$ or $NHR^5$;
$R^4$ is substituted or unsubstituted lower alkyl, lower alkylene, vinyl, aryl, aralkyl, cyanoaryl, carboalkoxyalkyl, alkoxyalkyl, alkoxyaryl, alkoxycarbonylalkyl, aminocarbonylalkyl, alkylcarbamoylalkyl, alkylthioalkyl, or alkylthioaryl;
$R^5$ is H, acetyl, or lower alkyl; and
$R^6$ is lower alkyl, dioxanyl, or thiodi-p-phenylene.

4. The emulsion concentrate of claim 3 wherein the aryl radicals are selected from the group consisting of substituted or unsubstituted phenyl, pyridinyl, pyrimidinyl, cyanophenyl, alkylthiophenyl, benzotriazinyl, phthalimidinyl, oxobenzoxazolyl, oxothiadiazolyl, carbalkoxybenzyl, morpholinocarbonylalkyl, nitrophenyl, oxobenzopyranyl, quinolyl, pyridazinyl, pyrazinyl, quinoxalinyl, pyrazolyl, triazolyl, and thiadiazolinonyl.

5. The emulsion concentrate of claim 1 wherein the organophosphorous insecticide is selected from the group consisting of:
  O,O-diethyl O-3,5-dibromo-6-chloro-2-pyridyl phosphorothioate,
  O,O-diethyl O-3,5,6-trichloro-2-pyridyl phosphorothioate,
  O,O-diethyl O-3,4,5,6-tetrachloro-2-pyridyl phosphorothioate,
  O,O-diethyl O-3,4,6-trichloro-2-pyridyl phosphorothioate,
  O,O-(thiodi-4,1-phenylene)bis(O,O-dimethyl phosphorothioate),
  O,6-ethoxycarbonyl-5-methyl pyrazolo 1,5-a pyrimidi-N-2-yl O,O-diethyl phosphorothioate,
  O-(4-bromo-2,5-dichlorophenyl)O,O-diethyl phosphorothioate,
  O,O-dimethyl-O-(2,5-dichloro-4-iodophenyl) phosphorothioate,
  O,O-diethyl O-2-quinoxalinyl phosphorothioate,
  O-2,6-dichloro-4-methyl phenyl O,O-dimethyl phosphorothioate,
  O,O-diethyl S-carboethoxymethyl phosphorodithioate,
  O,O-diethyl S-[(4-oxo-1,2,3-benzotriazin-3(4H)-yl) methyl]phosphorodithioate,
  O,O-dimethyl S-[(4-oxo-1,2,3-benzotriazin-3(4H)-yl) methyl]phosphorodithioate,
  S-(2-(formyl methyl aminol)-2-oxoethyl)O,O-dimethyl phosphorodithioate,
  O,O-dimethyl phosphorodithioate, S-ester with 4-(mercaptomethyl)-2-methoxy-1,3,4-thiadiazolin-5-one,
  O-ethyl S,S-dipropyl phosphorodithioate,
  O,O-diethyl-S-(N-isopropyl carbamoyl methyl) phosphorodithioate,
  O,O-dimethyl S-(2-((1-methyl carbamoyl ethyl)thio) ethyl)phosphorodithioate,
  O,S-dimethyl N-acetyl phosphoroamidothioate,
  O,O-bis(p-chlorophenyl)acetimidoyl-phosphoroamidothioate,
  O,S-dimethyl phosphoroamidothioate,
  O-butyl O-3,5-dichloro-2-pyridyl methyl phosphoroamidothioate,
  O-isopropyl O-3,5-dichloro-2-pyridyl methyl phosphoroamidothioate,
  O-sec-butyl O-3,5-dichloro-2-pyridyl methyl phosphoroamidothioate,
  O-isobutyl O-3,5-dichloro-2-pyridyl methyl phosphoroamidothioate,
  O-methyl O-3,5,6-trichloro-2-pyridyl isopropyl phosphoroamidothioate,
  O-methyl O-3,5-dibromo-2-pyridyl isopropyl phosphoroamidothioate,
  O-methyl O-3,5-dichloro-2-pyridyl isopropyl phosphoroamidothioate,
  O-methyl O-3,5-dibromo-2-pyridyl methyl phosphoroamidothioate,
  O-ethyl O-3,5-dibromo-2-pyridyl methyl phosphoroamidothioate,
  O-ethyl O-3,5-dichloro-2-pyridyl methyl phosphoroamidothioate,
  O-methyl O-3,5-dichloro-2-pyridyl methyl phosphoroamidothioate,
  O-methyl O-3,5-dichloro-2-pyridyl ethyl phosphoroamidothioate,
  O-ethyl O-3,5-dichloro-2-pyridyl-ethyl phosphoroamidothioate,
  O-isopropyl O-3,5-dibromo-2-pyridyl methyl phosphoroamidothioate,
  O-propyl O-3,5-dichloro-2-pyridyl methyl phosphoroamidothioate,
  O-propyl O-3,5-dichloro-2-pyridyl propyl phosphoroamidothioate,
  O-methyl O-3,4,6-trichloro-2-pyridyl isopropyl phosphoroamidothioate,
  propyl 3,5,6-trichloro-2-pyridyl methyl phosphoroamidate,
  methyl 3,5,6-trichloro-2-pyridyl isopropyl phosphoroamidate,
  O-p-cyanophenyl O-ethyl phenyl-phosphonothioate,
  O-ethyl O-(4-nitro phenyl)phenyl phosphonothioate, and
  O-ethyl S-phenyl ethyl phosphonodithioate.

6. The emulsion concentrate of claim 1 wherein the organophosphorous insecticide is O,O-diethyl O-(3,5,6-trichloro pyridine-2-yl)phosphorothioate.

7. The emulsion concentrate of claim 1 wherein the nonionic surfactant is selected from the group consisting of:
   1) block-polymeric polyether glycols;
   2) alkoxylated alkyl phenols;
   3) alkoxylated triglycerides;
   4) alkoxylated di- or tri-styryl phenols;
   5) alkoxylated sorbitol fatty esters;
   6) condensation products of alphatic alcohols with at least one alkylene oxide;
   7) condensation products of ethylene oxide with the products resulting from the reaction of propylene oxide and ethylene diamine;
   8) Ammonia, monoethanol and diethanol amides of acyl fatty acids;
   9) Semi-polar, long chain nonionics selected from the group consisting of
      i) tertiary amine oxides;
      ii) tertiary phosphine oxides; and
      iii) sulfoxides;
   10) polysiloxanes or alkoxylated polysiloxanes; and
   11) mixtures thereof.

8. The emulsion concentrate of claim 1 wherein the nonionic surfactant is selected from the group consisting of nonylphenol ethoxylated with 9 ethylene oxide moieties (9EO) per nonylphenol molecule; ethoxylated diamylphenol (9EO); ethoxylated tributylphenol (9EO); ethoxylated 2,4-ditertiary butyl phenol (9EO); and ethoxylated disecondary butylphenol (9EO).

9. The emulsion concentrate of claim 1 wherein the nonionic surfactant is selected from the group consisting of primary, secondary, and tertiary aliphatic alcohol ethoxylates.

10. The emulsion concentrate of claim 9 wherein the alcohol ethoxylate is a secondary aliphatic alcohol ethoxylate.

11. The emulsion concentrate of claim 1 wherein the nonionic surfactant is an ethoxylated trimethyl nonanol.

12. The emulsion concentrate of claim 1 wherein the nonionic surfactant is a polysiloxane or an alkoxylated polysiloxane.

13. A method of preparing organophosphorous insecticidal emulsion concentrates consisting essentially of the steps of:
   i) blending
      a) from about 10 to about 60 percent by weight of an organophosphorous insecticide having a melting point of less than about 120° C.;
      b) from about 20 to about 60 percent by weight of a water-soluble alkoxylated acid composition wherein said acid composition comprises:
         i) from greater than about 25 to about 60 percent by weight alkoxylated rosin acids; and
         ii) from about 40 to less than about 75 percent by weight alkoxylated fatty acids wherein the rosin acids and fatty acids have an average molar addition of from about 6 to about 20 alkoxy moieties per molecule of acid; the weight percents of the rosin and fatty acids being based on the total weight of said alkoxylated acids; and
      c) from about 15 to about 45 percent by weight of nonionic surfactant other than said alkoxylated rosin and alkoxylated fatty acids wherein said concentrate is essentially free of volatile organic compounds; and wherein the weight percents are based on the total weight of the emulsion concentrate except where indicated;
   ii) heating said nonionic surfactant to above the melting point either prior to, during, or after the blending; and
   iii) cooling the emulsion concentrate so formed to ambient temperature.

14. A method of preparing organophosphorous insecticidal emulsion concentrates consisting essentially of the steps of:
   i) melting from about 10 to about 60 percent by weight of an organophosphorous insecticide having a melting point of less than about 120° C.;
   ii) blending the molten insecticide with from about 20 to about 60 percent by weight of a water-soluble alkoxylated acid composition wherein said acid composition comprises:
      a) from greater than about 25 to about 60 percent by weight alkoxylated rosin acids; and
      b) from about 40 to less than about 75 percent by weight alkoxylated fatty acids wherein the rosin acids and fatty acids have an average molar addition of from about 6 to about 20 alkoxy moieties per molecule of acid; the weight percents of the rosin and fatty acids being based on the total weight of said alkoxylated acids; and
   iii) from about 15 to about 45 percent by weight of nonionic surfactant other than said alkoxylated rosin and alkoxylated fatty acids wherein said concentrate is essentially free of volatile organic compounds; and wherein the weight percents are based on the total weight of the emulsion concentrate except where indicated.

15. A method of controlling insects which comprises subjecting them to an insecticidally effective amount of a composition comprising the emulsion concentrate of claim 1.

16. A method of controlling insects which comprises subjecting them to an insecticidally effective amount of a composition comprising the emulsion concentrate of claim 2.

17. A method of controlling insects which comprises subjecting them to an insecticidally effective amount of a composition comprising the emulsion concentrate of claim 3.

18. A method of controlling insects which comprises subjecting them to an insecticidally effective amount of a composition comprising the emulsion concentrate of claim 4.

19. A method of controlling insects which comprises subjecting them to an insecticidally effective amount of a composition comprising the emulsion concentrate of claim 5.

20. A method of controlling insects which comprises subjecting them to an insecticidally effective amount of a composition comprising the emulsion concentrate of claim 6.

21. A method of controlling insects which comprises subjecting them to an insecticidally effective amount of a composition comprising the emulsion concentrate of claim 7.

22. A method of controlling insects which comprises subjecting them to an insecticidally effective amount of a composition comprising the emulsion concentrate of claim 8.

23. A method of controlling insects which comprises subjecting them to an insecticidally effective amount of a composition comprising the emulsion concentrate of claim 9.

24. A method of controlling insects which comprises subjecting them to an insecticidally effective amount of a composition comprising the emulsion concentrate of claim 10.

25. A method of controlling insects which comprises subjecting them to an insecticidally effective amount of a composition comprising the emulsion concentrate of claim 11.

26. A method of controlling insects which comprises subjecting them to an insecticidally effective amount of a composition comprising the emulsion concentrate of claim 12.

* * * * *